(12) United States Patent
Genta et al.

(10) Patent No.: US 8,163,517 B2
(45) Date of Patent: Apr. 24, 2012

(54) ORGANIC MATERIAL PRODUCTION SYSTEM USING BIOMASS MATERIAL AND METHOD

(75) Inventors: Minoru Genta, Hyogo (JP); Ryosuke Uehara, Hyogo (JP); Seiichi Terakura, Hyogo (JP); Kinya Fujita, Hyogo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 487 days.

(21) Appl. No.: 12/440,524

(22) PCT Filed: Oct. 2, 2008

(86) PCT No.: PCT/JP2008/067961
§ 371 (c)(1),
(2), (4) Date: Mar. 9, 2009

(87) PCT Pub. No.: WO2010/038302
PCT Pub. Date: Apr. 8, 2010

(65) Prior Publication Data
US 2011/0124057 A1    May 26, 2011

(51) Int. Cl.
*C12P 1/00* (2006.01)
*C12P 19/02* (2006.01)
*C12P 13/04* (2006.01)
*C12P 7/00* (2006.01)
*C12M 1/00* (2006.01)

(52) U.S. Cl. .......... 435/41; 435/105; 435/106; 435/132; 435/165; 435/289.1

(58) Field of Classification Search .................... 435/41, 435/105, 106, 165, 289.1, 132
See application file for complete search history.

(56) References Cited

FOREIGN PATENT DOCUMENTS

| | | |
|---|---|---|
| JP | 9-507386 A | 7/1997 |
| JP | 11-506934 A | 6/1999 |
| JP | 3042076 B2 | 5/2000 |
| JP | 2002-059118 A | 2/2002 |
| JP | 2002-59118 A | 2/2002 |
| JP | 2003-219900 A | 8/2003 |
| JP | 2005-027541 A | 2/2005 |
| JP | 2005-27541 A | 2/2005 |
| JP | 2005-168335 A | 6/2005 |
| JP | 2005-229821 A | 9/2005 |
| WO | 95/17517 A1 | 6/1995 |
| WO | 96/40970 A1 | 12/1996 |
| WO | 2010/038302 A1 | 4/2010 |

OTHER PUBLICATIONS

Biomass Ethanol, Up to 80% sachharification is possible, Nikkei Biotechnology & Business, Sep. 20, 2002, pp. 52-61.
International Search Report of PCT/JP2008/067961, date of mailing date Dec. 22, 2008.
International Search Report of PCT/JP2008/067961, Mailing Date of Dec. 22, 2008.

*Primary Examiner* — Herbert J Lilling
(74) *Attorney, Agent, or Firm* — Westerman, Hattori, Daniels & Adrian, LLP

(57) ABSTRACT

An organic material production system using biomass material includes: a hydrothermal decomposition apparatus (13) that causes the biomass material (11) and hot compressed water (12) to countercurrently contact with each other and undergo hydrothermal decomposition, and that transfers a lignin component and a hemicellulose component into the hot compressed water, so as to separate the lignin component and the hemicellulose component from a biomass solid residue; a cellulose enzymatic saccharification device (17) that treats, with an enzyme, cellulose in the biomass solid residue, so as to enzymatically saccharify the cellulose to a first sugar solution containing hexose; an alcohol fermenter (18) that produces alcohols by fermentation using the obtained first sugar solution; a sulfuric acid decomposition device (33) that decomposes, with sulfuric acid, the hemicellulose component in hot water (30) discharged from the hydrothermal decomposition apparatus, which contains the eluted lignin component and the eluted hemicellulose component, so as to decompose the hemicellulose component to a second sugar solution containing pentose; and a second alcohol fermenter (34) that produces, using the second sugar solution containing pentose, alcohols by fermentation.

4 Claims, 3 Drawing Sheets

ORGANIC MATERIAL PRODUCTION SYSTEM USING BIOMASS MATERIAL AND METHOD

TECHNICAL FIELD

The present invention relates to a biomass hydrothermal decomposition apparatus and a method thereof that enable efficient hydrothermal decomposition of biomass material, and to an organic material production system using biomass material, which system enables efficient production of organic materials such as alcohols, substitutes for petroleum, or amino acids by using such apparatus and method.

BACKGROUND ART

Technologies for producing ethanol or the like have been commercialized that involve converting woody biomass or other biomass into sugars with dilute sulfuric acid or concentrated sulfuric acid, and then subjecting them to solid-liquid separation, neutralizing the liquid phase thereof, and utilizing the resultant components as biomass materials for ethanol fermentation or the like (Patent Documents 1 and 2). Further, by using sugar as starting material, production of chemical industrial raw material (e.g., lactic fermentation) has been considered. Biomass as used herein refers to a living organism integrated in material circulation in the global biosphere or accumulation of organic materials derived from living organisms (see JIS K 3600 1258).

Sugarcane, corn, and other materials, currently used as alcohol raw materials, have been originally used for food. Using such food resources as long-term stable industrial resources is not preferable in view of life cycle of valuable food.

For this reason, it is a challenge to efficiently use cellulose resources such as herbaceous biomass and woody biomass, which are considered as potentially useful resources.

Cellulose resources include cellulose ranging from 38% to 50%, hemicelluloses components ranging from 23% to 32%, and lignin components, which are not used as fermentation materials, ranging from 15% to 22%. Due to many challenges, the industrial studies have been conducted targeting certain fixed materials, and no technologies have been disclosed yet on production systems taking into account diversity of the materials.

Production systems targeting fixed materials see almost no point regarding countermeasures for waste problems and global warming, because those systems have attempted such countermeasures with a method that brings more disadvantages to fermentation materials than starch materials. Thus, there has been a need for a method applicable to a variety of wastes in broader sense. Enzymatic saccharification methods are also considered as a future challenge due to its low efficiency. Acid treatment only achieves a low saccharification rate of about 75% (a basis for components that can be saccharified), due to excessive decomposition of sugar. Thus, the ethanol yield achieves only 25% by weight of cellulose resources (Non-Patent Document 1 and Patent Document 3).

[Patent Document 1] Japanese Patent Application Laid-open No. 9-507386
[Patent Document 2] Japanese Patent Application Laid-open No. 11-506934
[Patent Document 3] Japanese Patent Application Laid-open No. 2005-168335
[Non-Patent Document 1] Nikkei Biotechnology & Business, p. 52, September 2002
[Non-Patent Document 2] Biomass-Extensive Use of Bioresources, edited by Japanese Society for Bioscience, Biotechnology, and Agrochemistry, Asakura Publishing Co., Ltd., September 1985

DISCLOSURE OF INVENTION

Problem to be Solved by the Invention

In the proposals disclosed in Patent Documents 1 and 2 above, sulfuric acid necessary for reaction needs to be constantly supplied from outside the reaction system. With increasing the production scale, this poses problems, such as increasing the cost for purchasing equipment resistant to the acid and large amounts of sulfuric acid, while increasing the cost for disposing used sulfuric acid (e.g., cost for processing with a gypsum desulfulation), and the cost for recovering such sulfuric acid.

The proposal disclosed in Patent Document 3 above involves subjecting various types of cellulose resources to hydrothermal treatment, and converting them into sugars with enzymatic saccharification. During the hydrothermal treatment, cellulase inhibitors such as lignin components (Non-Patent Document 2) that inhibit enzymatic saccharification of cellulose are not removed and mixed with cellulose. This poses a problem of reducing the efficiency in cellulose enzymatic saccharification.

Other than cellulose, hemicellulose components are also contained in cellulose resources. This poses a problem that enzymes suitable for cellulose and hemicellulose components are necessary for enzymatic saccharification.

The resulting sugar solution includes a hexose solution from cellulose, and a pentose solution from hemicellulose components. For example, for alcohol fermentation, yeasts suitable for the respective solutions are necessary. Thus, alcohol fermentation needs to be improved low efficiency for fermenting a mixture of a hexose solution and a pentose solution.

As such, conventional technologies have caused a phenomenon that side reaction products inhibit enzymatic saccharification, reducing the sugar yield. Thus, what has been needed is a hydrothermal decomposition apparatus that removes inhibitors for enzymatic saccharification and thereby improves enzymatic saccharification of cellulose-based components.

In view of the foregoing problems, the present invention has an object to provide an organic material production system using biomass material, which can efficiently produce a sugar solution using such apparatus and method, and can efficiently produce various types of organic materials (e.g., alcohols, substitutes for petroleum, or amino acids) using the sugar solution as a base material.

Means for Solving Problem

According to an aspect of the present invention, an organic material production system using biomass material includes: a hydrothermal decomposition apparatus that causes the biomass material and hot compressed water to countercurrently contact with each other and undergo hydrothermal decomposition, and that transfers a lignin component and a hemicellulose component into the hot compressed water, so as to separate the lignin component and the hemicellulose component from a biomass solid residue; an enzymatic saccharification device that treats, with an enzyme, cellulose in the biomass solid residue discharged from the hydrothermal decomposition apparatus, so as to enzymatically saccharify the cellulose to a first sugar solution containing hexose; a first fermenter that produces, using the first sugar solution obtained by the first enzymatic saccharification device, any one of alcohols, substitutes for petroleum, or amino acids by fermentation; a sulfuric acid decomposition device that decomposes, with sulfuric acid, the hemicellulose component in hot water discharged from the hydrothermal decomposition apparatus, so as to decompose the hemicellulose component to a second sugar solution containing pentose; and a second fermenter that produces, using the second sugar solution obtained by the sulfuric acid decomposition device, any one of alcohols, substitutes for petroleum, or amino acids by fermentation.

Advantageously, in the organic material production system, the hydrothermal decomposition apparatus has a reaction temperature ranging from 180° C. to 240° C.

Advantageously, in the organic material production system, the sulfuric acid decomposition device has a decomposition temperature ranging from 100° C. to 140° C.

According to another aspect of the present invention, a method for organic material production using biomass material includes: a hydrothermal decomposition process that causes the biomass material and hot compressed water to countercurrently contact with each other and undergo hydrothermal decomposition; an enzymatic saccharification process that treats, with an enzyme, cellulose in the biomass solid residue discharged from the hydrothermal decomposition process, so as to enzymatically saccharify the cellulose to a first sugar solution containing hexose; a first fermentation process that produces, using the first sugar solution obtained by the first enzymatic saccharification process, any one of alcohols, substitutes for petroleum, or amino acids by fermentation; a sulfuric acid decomposition process that decomposes, with sulfuric acid, the hemicellulose component in hot water discharged from the hydrothermal decomposition process, so as to decompose the hemicellulose component to a second sugar solution containing pentose; and a second fermentation process that produces, using the second sugar solution obtained by the sulfuric acid decomposition device, any one of alcohols, substitutes for petroleum, or amino acids by fermentation.

Advantageously, in the method for organic material production, the hydrothermal decomposition process has a reaction temperature ranging from 180° C. to 240° C.

Advantageously, in the method for organic material production, the sulfuric acid decomposition process has a decomposition temperature ranging from 100° C. to 140° C.

Effect of the Invention

According to the present invention, with use of a hydrothermal decomposition apparatus that causes counter-current contact, side reaction products (lignin components and hemicellulose components) resulting from the reaction for producing a target component, i.e., cellulose, (that is enzymatically saccharified to a hexose solution) are transferred into the hot compressed water. In this way, the cellulose-based biomass solid residue can be obtained. Accordingly, by efficiently saccharifying it to the hexose solution and using the sugar solution as a base material, various types of organic materials (e.g., alcohols, substitutes for petroleum, or amino acids) can be produced efficiently. Further, the hemicellulose in the side reaction products, transferred to the hot water, is converted with sulfuric acid to monosaccharides at a low temperature, enabling liquid-liquid reaction with good efficiency.

Figure 1:
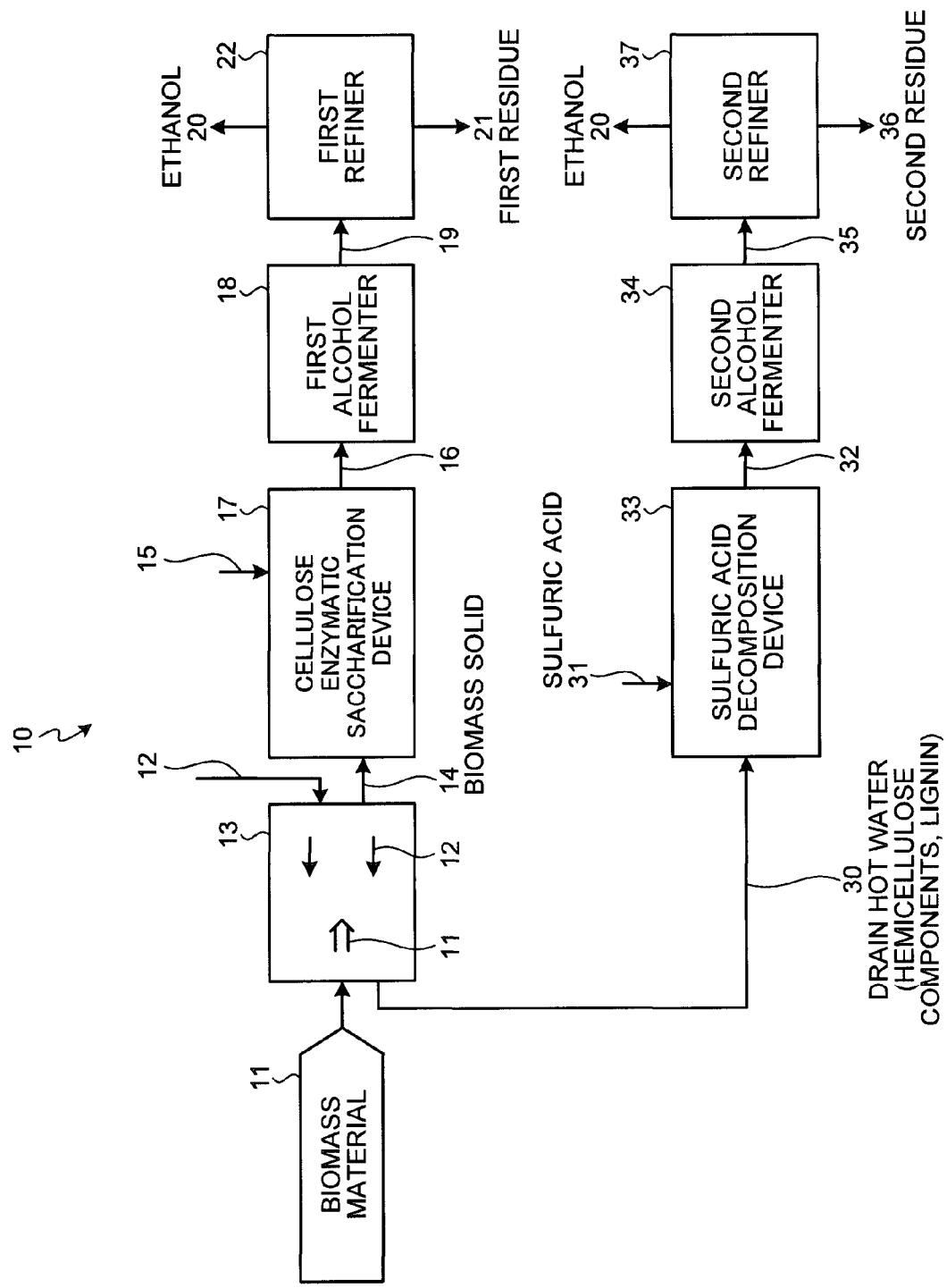
FIG. 1 is a schematic of an alcohol production system according to a first embodiment.

EXPLANATIONS OF LETTERS OR NUMERALS 10 alcohol production system
11 biomass material
12 hot compressed water
13 hydrothermal decomposition apparatus
14 biomass solid residue
15 enzyme
16 first sugar solution (hexose)
17 cellulose enzymatic saccharification device
18 first alcohol fermenter
19 first alcohol fermentation liquid
20 ethanol
21 first residue
22 first refiner
30 discharged hot water
31 sulfuric acid
32 second sugar solution (pentose)
33 sulfuric acid decomposition device
34 second alcohol fermenter
35 second alcohol fermentation liquid
36 second residue
37 second refiner

BEST MODE(S) FOR CARRYING OUT THE INVENTION

Exemplary embodiments of the present invention are described with reference to the accompanying drawings. The present invention is not limited to the embodiments. Constituting elements in the embodiments include elements easily achieved by a person skilled in the art, or elements being substantially equivalent to those elements.

First Embodiment

A system of producing an organic material, i.e., alcohol, with use of biomass material according to an embodiment of the present invention is described with reference to the drawings. FIG. 1 is a schematic of an organic material production system using biomass material according to the present embodiment. As shown in FIG. 1, an alcohol production system 10 using biomass material according to the present embodiment includes: a hydrothermal decomposition apparatus 13 that causes a biomass material 11 and hot compressed water 12 to countercurrently contact with each other and undergo hydrothermal decomposition, transfers lignin components and hemicellulose components into the hot compressed water 12, and separates the lignin components and the hemicellulose components from a biomass solid residue; a cellulose enzymatic saccharification device 17 that feeds an enzyme (cellulase) 15 into a biomass solid residue 14, which is discharged from the hydrothermal decomposition apparatus 13, and treats cellulose with the enzyme to enzymatically saccharify it to a first sugar solution 16 containing hexose; a first alcohol fermenter 18 that produces, using the first sugar solution (hexose) 16 obtained by the cellulose enzymatic saccharification device 17, an alcohol (ethanol in the present embodiment) by fermentation; a first refiner 22 that refines a first alcohol fermentation liquid 19, obtained by the first alcohol fermenter 18, so as to separate and refine it into a target product, i.e., ethanol 20, and a first residue 21; a sulfuric acid decomposition device 33 that discharges the hot compressed water 12, to which the lignin components and the hemicellulose components are transferred in the hydrothermal decomposition apparatus 13, as discharged hot water 30 to the outside, feeds sulfuric acid 31 to the discharged hot water 30, and decomposes with sulfuric acid the hemicellulose components in the discharged hot water 30, so as to produce a second sugar solution 32 containing pentose; a second alcohol fermenter 34 that produces, using the obtained second sugar solution (pentose) 32, an alcohol (ethanol in the present embodiment) by fermentation; and a second refiner 37 that refines a second alcohol fermentation liquid 35, so as to separate it into the target product, i.e., ethanol 20, and a second residue 36.

Biomass to be fed to the hydrothermal decomposition apparatus 13 is not limited to any specific type, and is a living organism integrated in material circulation in global biosphere or accumulation of organic materials derived from living organisms (see JIS K 3600 1258). In the present invention, particularly, cellulose resources of wood materials such as broadleaf trees and plant materials; agricultural wastes; and food wastes are preferably used.

The biomass material 11 is preferably broken into particles having a diameter of equal to or less than 5 millimeters for example, though not limited to this particle diameter. In the present embodiment, the pulverized biomass material 11 is used. Pretreatment equipment may be provided as necessary that breaks the biomass material 11 into particles having a diameter equal to or less than a predetermined diameter. When the biomass material 11 is chaff for example, the biomass material 11 can be fed to the hydrothermal decomposition apparatus 13 without being subjected to pulverization. Examples of pretreatment equipment may include cleaning equipment for cleaning biomass, as well as pulverizing equipment for controlling the particle diameter.

In the hydrothermal decomposition apparatus 13, the reaction temperature ranges from 180° C. to 240° C. preferably, and from 200° C. to 230° C. more preferably. This is because, at temperatures below 180° C., the hydrothermal decomposition takes place at a low rate and requires a longer time, increasing the apparatus size, which are not preferable. On the contrary, at temperatures above 240° C., the decomposition rate is too high and more cellulose components are transferred from the solid to the liquid, facilitating excessive decomposition of hemicellulose sugars, which are not preferable. Dissolution of cellulose components starts at about 140° C., dissolution of cellulose starts at about 230° C., and dissolution of lignin components starts at about 140° C. The temperature is preferably set within a range from 180° C. to 240° C. that allows cellulose to be remained in the solid, and that enables hemicellulose components and lignin components to be decomposed at adequate rates.

The reaction pressure of the hydrothermal decomposition is preferably set to a pressure higher by 0.1 MPa to 0.5 MPa than the saturated steam pressure of water at each temperature, which allows the hot compressed water to stay inside the device. The reaction time is preferably three minutes to ten minutes, not more than 20 minutes. This is because a longer reaction time increases the ratio of excessively decomposed products and is not preferable.

According to the present invention, for the flowage of the hot compressed water 15 and the flowage of the biomass material 11 inside the device main body 42A of the hydrothermal decomposition apparatus 41-1A, the hot compressed water 15 and the biomass material 11 are countercurrently contacted.

In the hydrothermal decomposition apparatus 13, the solid of the biomass material 11 is fed from the left side in the figure, while the hot compressed water 12 is fed from the right side in the figure. Because the biomass material 11 and the hot compressed water 12 move in an opposite direction to one another, the hot compressed water 12 (hot water, the liquid dissolving decomposed products) is moved while being soaked in solid particles by the counter-current flow against the solid, the biomass material 11.

When countercurrently contacting each other, the solid biomass material 11 is decomposed with the hot compressed water 12, and the resulting decomposed products are dissolved and transferred to the hot compressed water 12.

As a ratio of the solid to the liquid, the liquid ratio is preferably less, because it enables reduction in amount of water to be recovered and in amount of steam used for warming during the hydrothermal decomposition. The weight ratio of the biomass material and the hot compressed water both to be fed is, for example, 1:1 to 1:10 preferably, and 1:1 to 1:5 more preferably, though it varies accordingly depending on the apparatus configuration.

According to the present invention, in the hydrothermal decomposition apparatus 13, use of the counter-current flow transfers lignin components and hemicellulose components to the liquid, i.e., the hot compressed water 12, while allowing cellulose to remain in the solid, i.e., the biomass solid residue 14, to be discharged from the hydrothermal decomposition apparatus 13. In this way, the first sugar solution (hexose) 16 is obtained at the cellulose enzymatic saccharification device 17 for performing enzymatic saccharification. Accordingly, it is possible to establish a fermentation process suitable for a hexose (fermentation suitable for an end product: in the present embodiment, the ethanol 20 is obtained by fermentation using the first alcohol fermenter 18, and refined to the first alcohol fermentation liquid 19).

According to the present invention, with use of a hydrothermal decomposition apparatus that causes counter-current contact, side reaction products (lignin components and hemicellulose components) resulting from the reaction for producing a target component, i.e., cellulose, (that is enzymatically saccharified to a hexose solution) are transferred into the hot compressed water. In this way, the cellulose-based biomass solid residue can be obtained. Accordingly, by efficiently saccharifying the cellulose and using the sugar solution as a base material, various types of organic materials (e.g., alcohols) can be produced efficiently.

In the present invention, by causing counter-current contact, their components are sequentially discharged in order of solubility in the hot compressed water 12. Further, due to the temperature gradient from where the biomass is fed to where the hot water is fed, excessive decomposition of hemicellulose components is prevented. As a result, pentose components can be recovered efficiently. Further, by causing the biomass material and the hot compressed water to countercurrently contact with each other, the heat is recovered, which is preferable in view of system efficiency.

In the present embodiment, the ethanol 20 can be produced by fermentation, using the second sugar solution (pentose) 32 obtained by the sulfuric acid decomposition device 33.

As decomposition conditions in a sulfuric acid decomposition device according to the present invention, a sulfuric acid concentration is 0.1% by weight to 5% by weight, preferably 1% by weight to 4% by weight, a decomposition temperature is 100° C. to 140° C., preferably about 120° C., and a decomposition time is 30 minutes to three hours, preferably about one hour. This is because conditions outside these ranges result in unfavorable decomposition of hemicellulose.

In related art, when biomass material is decomposed with sulfuric acid without undergoing pretreatment, decomposition is carried out using sulfuric acid of 1% by weight for about 10 minutes at a high temperature of about 180° C. Because sulfuric acid acts as an inhibitor enzymatic saccharification of cellulose in downstream, the yield of hexose is low.

According to the present invention, the hydrothermal decomposition apparatus 13 causes cellulose components to remain in the biomass solid residue 14 in advance, and treats hemicellulose components, transferred to the hot compressed water 12, with sulfuric acid under a low temperature condition. This arrangement simplifies the configuration of the sulfuric acid equipment, and significantly reduces the use amount of sulfuric acid (0.6 time to 0.9 time the use amount of sulfuric acid in related art). As a result, the amount of sulfuric acid subjected to a disposal process (gypsum desulfuration process) is reduced, so that the equipment for recovering and separating sulfuric acid is downsized, reducing the equipment size.

Because the decomposition using sulfuric acid takes place at a temperatures equal to or less than 140° C., there is no need to prepare equipment resistant to the acid for a high temperature (180° C.) as in the related art, thus reducing the equipment cost.

When wheat straw was used as the biomass material 11 for example, the yields of recovered sugars achieve 0.85 for pentose (recovery rate 85%), and 0.91 for hexose (recovery rate 91%), assuming one for each of pentose and hexose in the wheat straw. As such, excellent recovery rates were achieved.

The discharged hot water 30 is not necessarily treated in a separate system. For example, processes subsequent to those performed at the enzymatic saccharification device 17 and sulfuric acid decomposition device 33, processes subsequent to those performed at the first and second alcohol fermenters 18, 34, or processes subsequent to those performed at the first and second refiners 22, 37 may be arranged as common processes, or other modification may be made appropriately.

According to the present invention, in the hydrothermal decomposition apparatus 13, use of the counter-current flow allows cellulose to remain in the solid phase which is the biomass solid residue 14. Accordingly, the first sugar solution (hexose) 16 is obtained by the enzymatic saccharification device 17 for performing enzymatic saccharification. Further, hemicellulose components dissolved in the liquid phase which is the hot compressed water 12, are separated as the discharged hot water 30, and the second sugar solution (pentose) 32 is obtained by the sulfuric acid decomposition device 33 using sulfuric acid. This enables the first sugar solution and the second sugar solution to be separated efficiently and saccharified in different processes. Accordingly, fermentation processes suitable for each of hexose and pentose (fermentation suitable for an end product: e.g., ethanol fermentation) can be established.

As such, in the hydrothermal decomposition apparatus 13, use of the counter-current flow transfers a side reaction product and a lignin component soluble in hot compressed water, both acting as inhibitors during enzymatic saccharification reaction for obtaining hexose, to the hot compressed water 12. Accordingly, the cellulose-based biomass solid residue 14 is obtained, improving the yield of the first sugar solution 16 containing pentose in the subsequent saccharification reaction by enzyme.

On the other hand, hemicellulose components contained in the separated discharged hot water 30 is saccharified later at the sulfuric acid decomposition device 33, so that a second sugar solution 32 containing pentose can be obtained. Then, in the first and second alcohol fermenters 18, 34 by using yeasts etc. suitable for hexose and pentose, ethanol 20 can be obtained by fermentation individually and efficiently.

Although the present embodiment describes an example that an alcohol, ethanol, is obtained by fermentation, the present invention is not limited to this example. Other than alcohols, substitutes for petroleum used as chemical product material, or amino acids used as food and feed materials can be obtained with a fermenter.

Examples of industrial products produced from a sugar solution as a base material may include liquefied petroleum gas (LPG), auto fuel, aircraft jet fuel, heating oil, diesel oil, various types of heavy oils, fuel gas, naphtha, and naphtha decomposed products such as ethylene glycol, ethanolamine, alcohol ethoxylate, vinyl chloride polymer, alkylaluminum, polyvinyl acetate (PVA), vinyl acetate emulsion, polystyrene, polyethylene, polypropylene, polycarbonate, methyl methacrylate (MMA) resin, nylon, and polyester. Thus, substitutes for industrial products derived from crude oil, which is fossil fuel, and sugar solution derived from biomass, which is a material for producing such substitutes, can be used efficiently.

As described above, the present invention provides: an organic material production system and a method using biomass material that can produce, by transferring cellulose-based components and hemicellulose components from the biomass material to the hot compressed water and separating them from each other, sugar solutions suitable for the cellulose-based components and the himicellulose components (hexose sugar solution and pentose sugar solution), and that can efficiently produce, using the sugar solutions as base materials, various types of organic materials (e.g., alcohols, substitutes for petroleum, or amino acids). However, a conventional technology causes a phenomenon that a side reaction product inhibits enzymatic saccharification and a sugar yield is reduced.

Second Embodiment

Figure 2:
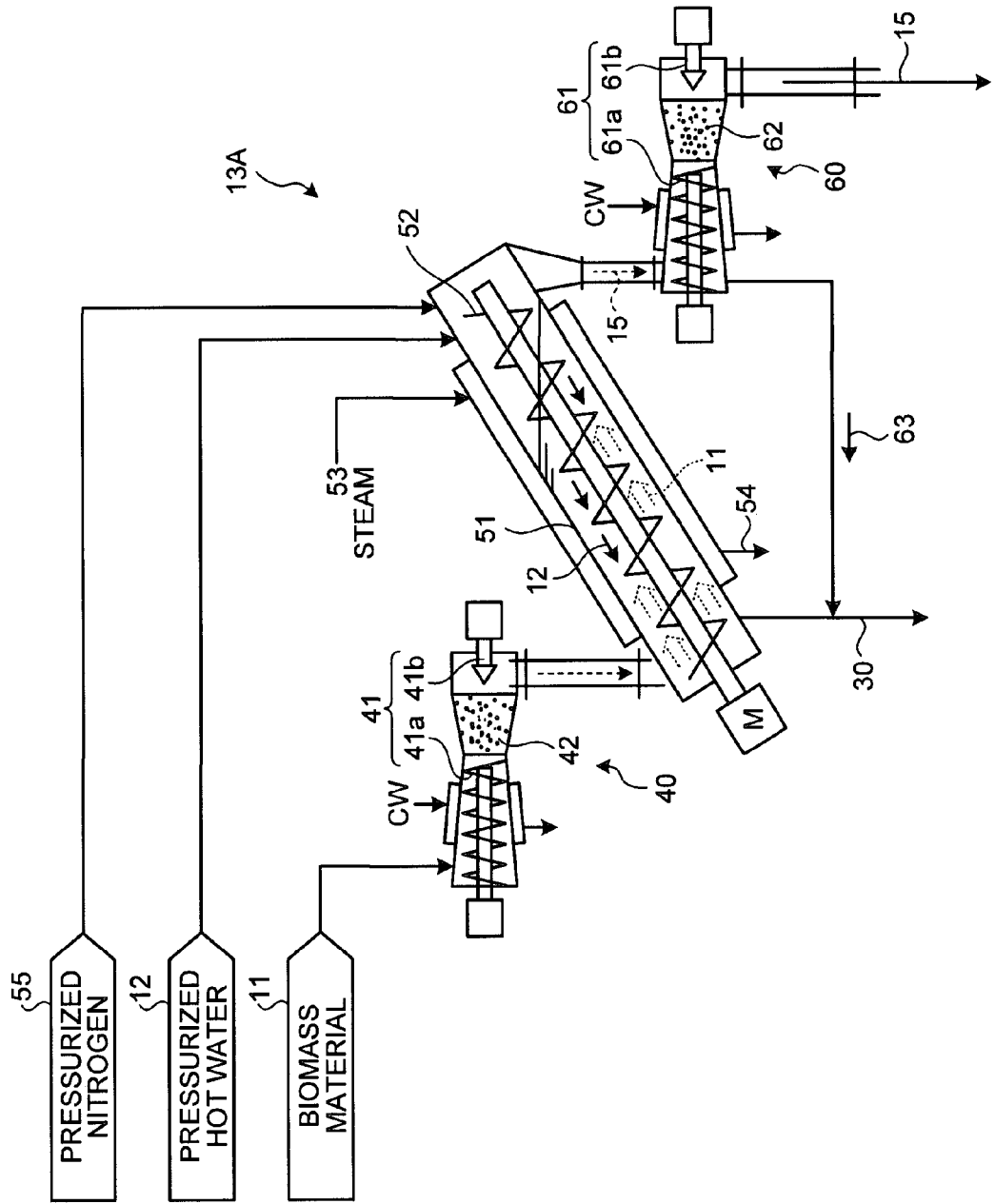
FIG. 2 is a schematic of a hydrothermal decomposition apparatus according to a second embodiment.

With reference to the drawings, the following describes an embodiment of a biomass thermal decomposition apparatus used in the alcohol production system 10 using biomass material according to the present invention. FIG. 2 is a schematic of a biomass hydrothermal decomposition apparatus according to the embodiment. As shown in FIG. 2, a biomass hydrothermal decomposition apparatus 13A according to the present embodiment includes: a biomass feeder 40 that feeds a biomass material 11 under normal pressure to under increased pressure; the hydrothermal decomposition apparatus 13A that allows the fed biomass material (e.g., wheat straw in the present embodiment) 11 to be gradually conveyed inside a slanted device main body (hereinafter, "device main body") 51 from a lower end thereof with a conveyor screw 52, and also allows hot compressed water 12 to be fed into the device main body 51 from an upper end thereof, which is different from a feed section for the biomass material 11, so as to cause the biomass material 11 and the hot compressed water 12 to countercurrently contact with each other and undergo hydrothermal decomposition, and that transfers lignin components and hemicellulose components into the hot compressed water 12, so as to separate the lignin components and the hemicellulose components from the biomass material 11; and a biomass discharger 60 that discharges a biomass solid residue 14 under increased pressure to under normal pressure, at the upper end of the device main body 51. In the figure, indicated by a reference numeral 53 is steam, 54 is a drain, and 55 is pressurized nitrogen.

As such, with use of the slanted hydrothermal decomposition apparatus 13A, the biomass material 11 and the hot compressed water 12 countercurrently contact with each other inside the apparatus. Accordingly, side reaction products (lignin components and hemicellulose components) resulting from the hydrothermal reaction for producing a target component, i.e., cellulose, (that is enzymatically saccharified to a hexose solution) are transferred into the hot compressed water 12. In this way, the cellulose-based biomass solid residue 14 can be obtained. Accordingly, by efficiently saccharifying the cellulose to the first sugar solution containing hexose and using the sugar solution as a base material, various types of organic materials (e.g., alcohols) can be produced efficiently. On the other hand, the hemicellulose components in the discharged hot water 30, discharged from the hydrothermal decomposition apparatus 13A, are degraded by sulfuric acid decomposition to a second sugar solution containing pentose and using the sugar solution as a base material, various types of organic materials (e.g., alcohols) can be efficiently produced.

In the present embodiment, the biomass material 11 is fed from the lower end. The present invention is not limited to this, and the biomass material 11 may be fed from the upper end reversely. In this case, the hot compressed water 12 is fed from the lower end. Examples of the biomass feeder 40 that feeds biomass under normal pressure to under increased pressure may include a pump unit such as a piston pump or a slurry pump.

In the present embodiment, the hydrothermal decomposition apparatus 13A is a slanted type apparatus as shown in FIG. 2. The present invention is not limited to this, and a vertical or horizontal hydrothermal decomposition reaction apparatus may be adopted.

The hydrothermal decomposition apparatus may be arranged as a slanted type or a vertical type, because it is preferable regarding that the gas resulting from the hydrothermal decomposition reaction, the gas brought into the material, and the like can be released quickly from the upper side. This arrangement is also preferable in view of the discharging efficiency, because decomposed products are discharged with the hot compressed water 12 and therefore the concentration of the discharged materials is increased from the upper side to the lower side.

According to a hydrothermal decomposition apparatus 13A of the embodiment, by providing the conveyor screw 52, 1) the delivery of the solid is possible by the counter-current flow of solid and liquid, 2) the solid-liquid separation is possible inside the device main body 51, and 3) the hot compressed water on the surface of the solid and inside the solid is progressively mixed inside the device main body 51, so that the reaction is facilitated.

The conveyor screw 52 may include a scraper (not shown) that prevents occlusion of an outlet for discharged hot water 30.

According to the present embodiment, in a slurry transport reactor that mixes the biomass material 11 and water in advance and feeds the mixture into the device main body, water needs to be added in large amounts (10 times to 20 times in weight ratio) relative to the solid so as to provide flowability to the slurry. However, because the material, i.e., the biomass material 11, and the hot compressed water 12 for removing lignin components and hemicelullose components in the biomass are fed into the hydrothermal decomposition apparatus 13A with separate systems, the weight ratio of the liquid can be made small relative to that of the solid, thus improving economic efficiency.

According to the present invention, because a gas portion is present inside the device main body 51, pressurized nitrogen ($N_2$) 55 is fed inside.

Inside the hydrothermal decomposition apparatus 13A, the temperature of the biomass material 11 is increased by causing it to contact the hot compressed water 12 in the device main body 51 and directly exchanging the heat. The temperature may be increased by using steam or the like from the outside as necessary.

The biomass feeder 40 employs a screw feeding mechanism 41 that has a material seal mechanism realized by the biomass itself, and feeds the solid biomass material 11 under normal pressure to under increased pressure. Specifically, with the feeding mechanism 41 including a screw feeder 41a and a hydraulic cylinder 41b, the biomass material 11 fed inside is compressed, so that a biomass plug 42 is formed. The biomass plug 42 serves as a material seal for keeping the pressure inside the hydrothermal decomposition apparatus 13A. Gradually pressed by the screw feeder 41a, the biomass can be gradually discharged from an edge of the hydraulic cylinder 41b, so that the biomass material 11 is reliably fed into the device main body 51.

The biomass discharger 60 has a similar configuration to that of the biomass feeder 40. With a feeding mechanism 61 including a screw feeder 61a and a hydraulic cylinder 61b, the biomass solid residue 14 reacted in the hydrothermal decomposition apparatus is compressed, so that a biomass plug 62 is formed. The biomass plug 62 serves as a material seal for keeping the pressure inside the hydrothermal decomposition apparatus 13A. The biomass solid residue 14 under increased pressure, from which lignin components and hemicellulose components have been transferred to the discharged hot water 30, can be discharged to under normal pressure. When discharged, the residual water is removed from the biomass plug 62. This dewatered solution 63 includes components soluble in hot compressed water (lignin components and hemicellulose components). Thus, the dewatered solution 63 is sent to the discharged hot water 30 and treated together with the discharged hot water 30.

Because the pressure is changed from increased pressure to normal pressure inside the biomass discharger 60, the discharged biomass solid residue 14 is steam-exploded, causing breakage of its fiber. This improves the efficiency of enzymatic saccharification in the subsequent process.

The biomass discharger 60 can remove both of enzymatic saccharification inhibitors and ethanol fermentation inhibitors, or either of them, which are low-molecular-weight volatile inhibitors.

In the present invention, by causing biomass material and hot compressed water to countercurrently contact with each other, their components are sequentially eluted in order of solubility in the hot water. Further, due to the temperature gradient from where the biomass is fed to where the hot water is fed, excessive decomposition of hemicellulose components is prevented. As a result, pentose components can be recovered efficiently. Further, by causing the biomass material and the hot compressed water to countercurrently contact with each other, the heat is recovered, which is preferable in view of system efficiency.

Third Embodiment

Figure 3:
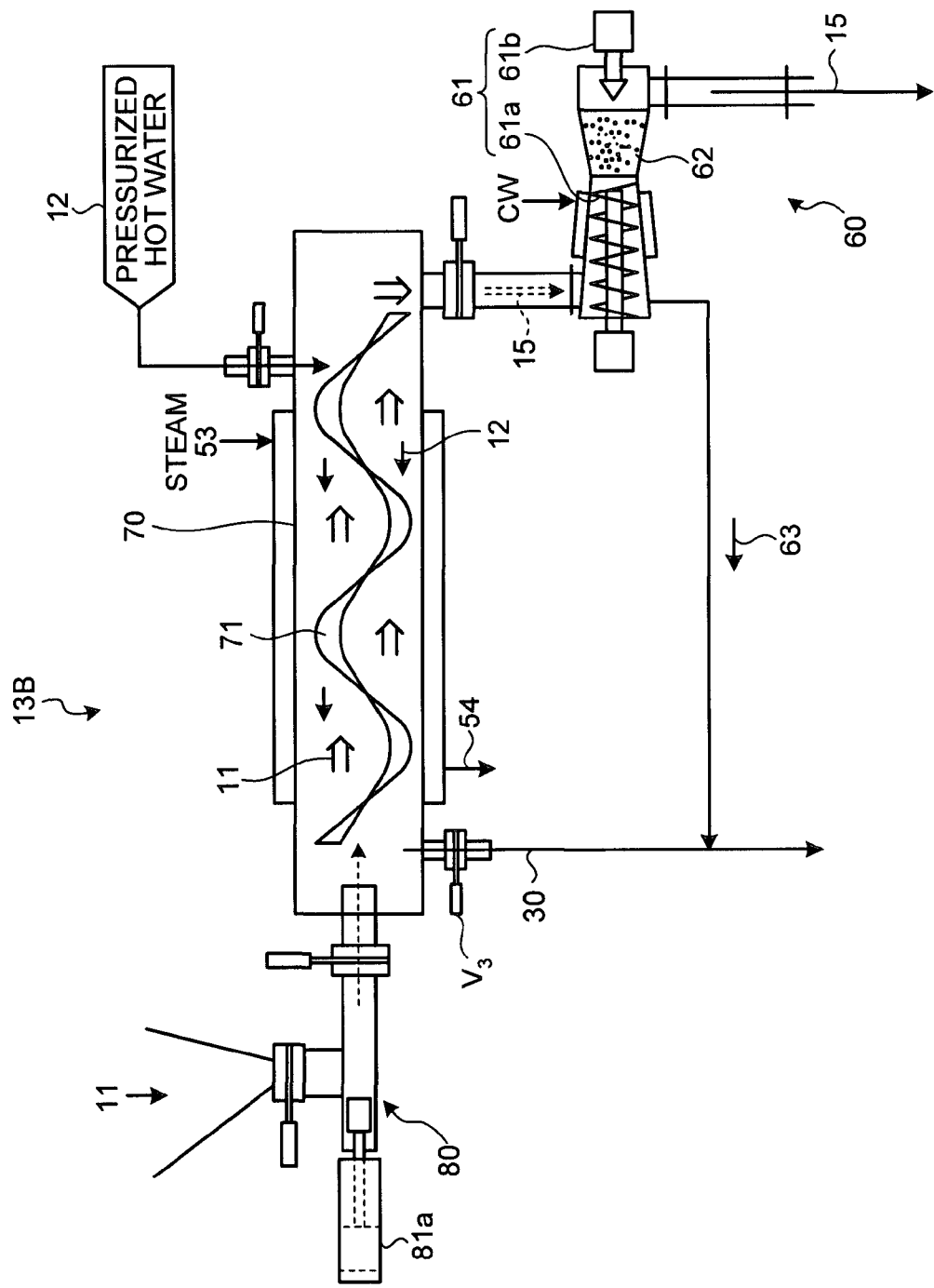
FIG. 3 is a schematic of a hydrothermal decomposition apparatus according to a third embodiment.

With reference to the drawings, the following describes another embodiment of the biomass hydrothermal decomposition apparatus used in the alcohol production system 10 using biomass material according to the present invention. FIG. 3 is a schematic of a biomass hydrothermal decomposition apparatus according to the present embodiment. As shown in FIG. 3, a biomass hydrothermal decomposition apparatus 13B according to the present embodiment includes: a biomass feeder 80 that feeds the biomass material (e.g., wheat straw in the present embodiment) 11 under normal pressure to under increased pressure; a horizontal device main body (hereinafter, "device main body") 70 that allows the fed biomass material 11 to be gradually moved therethrough from an end on either the left or the right side (on the left side in the present embodiment) thereof in a consolidated condition, and also allows the hot compressed water 12 to be fed therein from an end (on the right side in the present embodiment), which is different from the side from which the biomass material 11 is fed, so as to cause the biomass material 11 and the hot compressed water 12 to countercurrently contact with each other and undergo hydrothermal decomposition, and that transfers lignin components and hemicellulose components into the hot compressed water 12, so as to separate the lignin components and the hemicellulose components from the biomass material 11; and the biomass discharger 60 that discharges the biomass solid residue 14 under increased pressure to under normal pressure, at the side from which the hot compressed water 12 is fed into the device main body 70. Examples of the biomass feeder 80 that feeds biomass under normal pressure to under increased pressure may include a pump unit such as a piston pump or a slurry pump.

In the present embodiment, inside the device main body 70 is provided a fixed stirring unit 71 that stirs the biomass material 11 in a consolidated condition, so called in plug flow. With this arrangement, the biomass material 11 fed therein is stirred by stirring action when moved axially.

By providing the fixed stirring unit 71, the hot compressed water 12 on the surface of the solid and inside the solid is progressively mixed in the device main body 70, so that the reaction is facilitated.

According to the present invention, for the flowage of the hot compressed water 12 and the flowage of the biomass material 11 inside the device main body 70 of the hydrothermal decomposition apparatus 13B, the hot compressed water 12 and the biomass material 11 are countercurrently contacted, preferably with agitated flow.

The hydrothermal decomposition apparatus 13B performs decomposition in plug flow and has a simple configuration. Thus, the solid, the biomass material 11 is moved parallel to a central axis of its pipe, while being stirred in a direction perpendicular to the central axis of the pipe. On the contrary, the hot compressed water 12 (hot water, the liquid dissolving decomposed products) is moved while being soaked in solid particles by the counter-current flow against the solid.

In the plug flow, the hot compressed water 12 is flowed uniformly. This is because, when the solid biomass material 11 is decomposed in the hot compressed water 12, the decomposed products are dissolved in the hot water. Accordingly, the viscosity around a decomposed portion is increased, so that the hot water is moved toward an undecomposed portion dominantly, causing decomposition of the undecomposed portion. This creates a uniform flow of the hot water, enabling uniform decomposition.

In the device main body 70 of the hydrothermal decomposition apparatus 13B, due to the resistance of its inner pipe wall, the solid density at the outlet side for the biomass material 11 is reduced compared with that at the inlet side for the biomass material 11. In addition, the amount of the biomass solid residue 14 is reduced by the decomposition. As a result, the ratio of the hot compressed water 12 is increased, and the liquid retention time is prolonged, causing excessive decomposition of decomposed components in the liquid. For this reason, the fixed stirring unit is provided as appropriate.

The fixed stirring unit 71 may have grooves formed thereon, or may be installed at various pitches. Further, the fixed stirring unit 71 may have screws in series at multiple stages, so that each screw performs stirring individually. The device main body 70 of the hydrothermal decomposition apparatus 13B may have a taper shape. Specifically, in the device main body 70, the outlet for the biomass material 11 may have a smaller cross-sectional area than the inlet. With this arrangement, the solid density of the biomass material 11 is increased in the device main body 70.

Further, an unstiffing function may be provided for preventing the solid from occluding the device main body 70. Further, the solid-liquid weight ratio in the device main body 70 may be controlled appropriately by controlling, for example, the torque of a rotating stirring unit, the capacitance and the ultrasonic wave in the device main body 70, and the weight of components inside the device main body 70.

The hot compressed water 12 is flowed by the counter-current flow, so that the heat is directly exchanged. This prevent excessive decomposition of decomposed products (such as lignin components), which are decomposed and discharged into the liquid phase.

The hot compressed water 12 to be fed into the device main body 70 is preferably less in weight relative to the biomass material 11, because it enables reduction in amount of steam used for warming during the hydrothermal decomposition. The weight ratio of the biomass material 11 to the hot compressed water 12 both to be fed is, for example, 1:1 to 1:10 preferably, and 1:1 to 1:5 more preferably, though it varies accordingly depending on the apparatus configuration. Particularly, in the present embodiment, the plug flow is composed of solid phase and liquid phase, i.e. the biomass material and the hot compressed water, and is moved through the device main body 70 in the consolidated condition. The solid-to-liquid ratio can, therefore, be 1:1 to 1:5. As described, the weight ratio of the biomass material 11 and the hot compressed water 12 both to be fed into the device main body 70 is made 1:1 to 1:10, thereby reducing the heat necessary for the hydrothermal decomposition apparatus.

Further, by controlling the solid-to-liquid weight ratio inside the device main body 70, the conditions for hydrothermal decomposition are stabilized, and the biomass solid residue 14 is stably discharged from the biomass discharger 60.

By causing the biomass material 11 and the hot compressed water 12 to countercurrently contact with each other inside the hydrothermal decomposition apparatus 13B, the solid-liquid separation is performed. This reduces the amount of excessively decomposed products to be brought into the solid, cellulose. Because lignin components and the like are precipitated at low temperatures, the separation is difficult at low temperatures. Thus, after the hydrothermal decomposition, the decomposed products are taken out from the reaction system and subjected to the separation. In this way, it is possible to reduce the heat loss when flush occurs due to a transition from a high temperature and high pressure condition to a normal temperature and normal pressure condition. Further, the discharging liquid containing the decomposed products is separated with improved efficiency. This arrangement is realized considering the fact that the hydrothermal decomposition products are polysaccharide components precipitated at low temperatures and therefore the separation is hardly carried out at low temperatures.

According to the present embodiment, the weight of the biomass material 11 to be fed into the hydrothermal decomposition apparatus 13B is increased, relative to the weight of the hot compressed water 12. This enables reduction in the apparatus size, thus contributing to improve economic efficiency.

Inside the hydrothermal decomposition apparatus 13B, the temperature of the biomass material 11 is increased by causing it to contact the hot compressed water 12 in the device main body 70 and directly exchanging the heat. The temperature may be increased by using steam 53 or the like from the outside as necessary. Alternatively, saturated steam may be directly fed into the device main body 42, instead of the hot water.

In the present embodiment, the biomass feeder 80 employs a mechanism for feeding the biomass material 11, including a piston pump 81a. With this arrangement, the biomass feeder 80 feeds the solid biomass material 11 under normal pressure to under increased pressure. By using the piston pump 81a and applying pressure with the piston, the biomass material 11 is reliably fed into the device main body 70.

Specifically, use of the piston pump 81a enables the solid in the counter-current flow of solid and liquid, i.e., the biomass material 11, to be moved by operation of the piston pump 81a, without providing a rotational moving unit or the like for moving the solid inside the device main body 70. Further, use of the piston pump 81a also enables control of the density inside the device main body 70 (the solid-to-liquid weight ratio). Specifically, it is possible to control the retention time of the hot compressed water inside the device main body 70.

The biomass discharger 60 is the same as that in the hydrothermal decomposition apparatus 13A shown in FIG. 2, and thus descriptions thereof are omitted.

In the present embodiment, the hot compressed water 12 is discharged at a portion near the inlet for feeding the biomass. Alternatively, a liquid outlet for the hot compressed water 12 may be provided in a middle portion and the discharged liquid may be subjected to both of heating and cooling, or either of them, so that an ideal temperature distribution is plotted. Then, the discharged liquid may be fed into the device main body 70 again.

The concentration of inhibitors such as furfral in the liquid may be measured near a discharge section for the hot compressed water 12, so that the feed amount of the hot compressed water 12 is controlled based on the measured value. Or, the sugar concentration may be measured near the biomass discharger 60, so that the feed amount of the hot compressed water 12 is controlled based on the measured value.

In the present embodiment, the hot compressed water 12 may be fed from one section. The present invention is not limited to this, and the hot compressed water 12 may be fed from a plurality of sections for temperature control.

In the present invention, by causing biomass material and hot compressed water to countercurrently contact with each other, their components are sequentially discharged in order of solubility in the hot water. Further, due to the concentration gradient and the temperature gradient from where the biomass is fed to where the hot water is fed, excessive decomposition of hemicellulose components is prevented. As a result, pentose components can be recovered efficiently. Further, by causing the biomass material and the hot compressed water to countercurrently contact with each other, the heat is recovered, which is preferable in view of system efficiency.

According to a modification of the present embodiment, the horizontal hydrothermal decomposition apparatus 13B as shown in FIG. 3 may be arranged as a slanted type or a vertical type. The device main body may be arranged as a slanted type or a vertical type, because it is preferable regarding that the gas resulting from the hydrothermal decomposition reaction, the gas brought into the material, and the like can be released quickly from the upper side. This arrangement is also preferable in view of the discharging efficiency, because decomposed products are discharged with the hot compressed water 12 and therefore the concentration of the discharged materials is increased from the upper side to the lower side.

INDUSTRIAL APPLICABILITY

As described, the system and method according to the present invention can separate cellulose-based components from biomass material, so as to efficiently produce a sugar solution. Further, using the sugar solution as a base material, various types of organic materials (e.g., alcohols, substitutes for petroleum, or amino acids) can be efficiently produced.

The invention claimed is:

1. An organic material production system using biomass material, the organic material production system comprising:
    a hydrothermal decomposition apparatus that causes the biomass material and hot compressed water to countercurrently contact with each other and undergo hydrothermal decomposition, and that transfers a lignin component and a hemicellulose component into the hot compressed water, so as to separate the lignin component and the hemicellulose component from a biomass solid residue;
    an enzymatic saccharification device that treats, with an enzyme, cellulose in the biomass solid residue discharged from the hydrothermal decomposition apparatus, so as to enzymatically saccharify the cellulose to a first sugar solution containing hexose;
    a first fermenter that produces, using the first sugar solution obtained by the first enzymatic saccharification device, any one of alcohols, substitutes for petroleum, or amino acids by fermentation;
    a sulfuric acid decomposition device that decomposes, with sulfuric acid, the hemicellulose component in hot water discharged from the hydrothermal decomposition apparatus, so as to decompose the hemicellulose component to a second sugar solution containing pentose; and
    a second fermenter that produces, using the second sugar solution obtained by the sulfuric acid decomposition device, any one of alcohols, substitutes for petroleum, or amino acids by fermentation,
    wherein the hydrothermal decomposition device has a reaction temperature ranging from 180° C. to 240° C. and has a condition of hot compressed water, and
    wherein the sulfuric acid decomposition device has a decomposition temperature ranging from 100° C. to 140° C.

2. A method for organic material production using biomass material, the method comprising:
    a hydrothermal decomposition process that causes the biomass material and hot compressed water to countercurrently contact with each other and undergo hydrothermal decomposition;
    an enzymatic saccharification process that treats, with an enzyme, cellulose in the biomass solid residue discharged from the hydrothermal decomposition process, so as to enzymatically saccharify the cellulose to a first sugar solution containing hexose;
    a first fermentation process that produces, using the first sugar solution obtained by the first enzymatic accharification process, any one of alcohols, substitutes for petroleum, or amino acids by fermentation;

a sulfuric acid decomposition process that decomposes, with sulfuric acid, the hemicellulose component in hot water discharged from the hydrothermal decomposition process, so as to decompose the hemicellulose component to a second sugar solution containing pentose; and a second fermentation process that produces, using the second sugar solution obtained by the sulfuric acid decomposition device, any one of alcohols, substitutes for petroleum, or amino acids by fermentation, wherein a reaction temperature of the hydrothermal decomposition ranges from 180° C. to 240° C., and wherein the sulfuric acid decomposition process has a decomposition temperature ranging from 100° C. to 140° C.

3. An organic material production system using biomass material, the organic material production system comprising:

a hydrothermal decomposition apparatus that causes the biomass material and hot compressed water to countercurrently contact with each other and undergo hydrothermal decomposition, and that transfers a lignin component and a hemicellulose component into the hot compressed water, so as to separate the lignin component and the hemicellulose component from a biomass solid residue;

an enzymatic saccharification device that treats, with an enzyme, cellulose in the biomass solid residue discharged from the hydrothermal decomposition apparatus, so as to enzymatically saccharify the cellulose to a first sugar solution containing hexose; and a sulfuric acid decomposition device that decomposes, with sulfuric acid, the hemicellulose component in hot water discharged from the hydrothermal decomposition apparatus, so as to decompose the hemicellulose component to a second sugar solution containing pentose;

a second fermenter that produces, using the second sugar solution obtained by the sulfuric acid decomposition device, any one of alcohols, substitutes for petroleum, or amino acids by fermentation, wherein the hydrothermal decomposition device has a reaction temperature ranging from 180° C. to 240° C. and has a condition of hot compressed water, and wherein the sulfuric acid decomposition device has a decomposition temperature ranging from 100° C. to 140° C.

4. A method for organic material production using biomass material, the method comprising:

a hydrothermal decomposition process that causes the biomass material and hot compressed water to countercurrently contact with each other and undergo hydrothermal decomposition; an enzymatic saccharification process that treats, with an enzyme, cellulose in the biomass solid residue discharged from the hydrothermal decomposition process, so as to enzymatically saccharify the cellulose to a first sugar solution containing hexose; and a sulfuric acid decomposition process that decomposes, with sulfuric acid, the hemicellulose component in hot water discharged from the hydrothermal decomposition process, so as to decompose the hemicellulose component to a second sugar solution containing pentose, wherein a reaction temperature of the hydrothermal decomposition ranges from 180° C. to 240° C., and wherein the sulfuric acid decomposition process has a decomposition temperature ranging from 100° C. to 140° C.

* * * * *